United States Patent
Weissel et al.

[11] 3,933,924
[45] Jan. 20, 1976

[54] PROCESS FOR PREPARING HYDROXYDIPHENYL

[75] Inventors: Oskar Weissel, Krefeld; Horst Köller, Krefeld-Veeberg; Hans-Helmut Schwarz, Krefeld, all of Germany

[73] Assignee: Bayer Aktiengesellschaft, Leverkusen, Germany

[22] Filed: Mar. 11, 1974

[21] Appl. No.: 450,252

[30] Foreign Application Priority Data
Mar. 26, 1973 Germany............................ 2314950

[52] U.S. Cl. ................................................ 260/620
[51] Int. Cl.² ........................................ C07C 37/06
[58] Field of Search ............ 260/620; 252/440, 443

[56] References Cited
UNITED STATES PATENTS

| | | | |
|---|---|---|---|
| 1,862,000 | 6/1932 | Britton et al. | 260/620 |
| 2,708,208 | 5/1955 | Furman et al. | 260/620 |
| 3,637,870 | 1/1972 | Berthoux et al. | 260/620 |
| 3,697,606 | 10/1972 | Freudewald et al. | 260/620 |

*Primary Examiner*—Norman Morgenstern
*Attorney, Agent, or Firm*—Burgess, Dinklage & Sprung

[57] ABSTRACT

Hydroxydiphenyl is prepared by dehydrogenating a starting material comprising completely and/or partly hydrogenated hydroxydiphenyl in a gaseous phase in the presence of a dehydrogenation catalyst and a compound having the formula

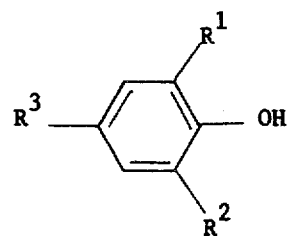

wherein
$R^1$, $R^2$ and $R^3$, which may be the same or different, each represents a linear or optionally branched alkyl radical having up to 6 carbon atoms, in addition to which $R^3$ can also represent a hydrogen atom, is added as a stabilizer to the starting material before it comes into contact for the first time with and and/or other oxygen-containing gases.

5 Claims, No Drawings

PROCESS FOR PREPARING HYDROXYDIPHENYL

BACKGROUND

This invention relates to a process for the production of hydroxydiphenyl.

Hydroxydiphenyl is known to be obtained by catalytically dehydrogenating compounds or mixtures of compounds comprising completely and/or partially hydrogenated hydroxydiphenyl, in the gaseous phase. The dehydrogenation catalysts used for this purpose contain nickel, chromium, aluminium, copper and alkali oxide or carbonate and, in some cases, silver and are described, for example, in German Patent No. 1,108,221 and DOS No. 2,049,809.

In addition to hydroxydiphenyl, a number of secondary products and intermediate products, principally phenol, diphenyl and cyclohexylphenol and, to some extent, diphenylene oxide, are formed in this dehydrogenation process and have to be removed by special purification processes, for example the process described in DOS No. 2,102,476. However, the reaction product to be purified must satisfy certain qualitative requirements if a purification process of this kind is to be carried out successfully both from the technical and the economic standpoint. The main requirement is that the reaction product to be purified should have as uniform a qualitative and quantitative composition as possible.

On the other hand, the activity of the dehydrogenation catalyst is known to decrease with time so that the conversion is reduced and the composition of the reaction product is altered accordingly. Although this change in composition can be counteracted by reducing the catalyst load and/or by increasing the reaction temperature, reduction of the catalyst load involves a reduction in throughput and, hence, has an adverse effect upon the dehydrogenation process, whilst increasing the reaction temperature promotes secondary reactions to a greater extent than the main reaction, resulting in a deterioration in the composition of the reaction product.

For this reason, the continuous process has to be interrupted after a certain time in order to regenerate or replace the catalyst. However, this again involves a reduction in the output of the installation in which the process is carried out, quite apart from increased costs.

It has also proved to be advantageous to use a crude dehydrogenation product of substantially constant composition for purification. As already mentioned, however, it is not possible to obtain a crude product of this kind by conventional dehydrogenation processes. Although it is possible, by storing and mixing dehydrogenation products of different composition in an intermediate stage, to prepare a product of constant composition for the purification process, this involves more work and additional costs.

In order to obviate the disadvantages attending conventional dehydrogenation processes, there is an urgent need for a dehydrogenation process which gives a dehydrogenation product remaining uniform in its composition over prolonged periods without any appreciable change in the activity and selectivity of the dehydrogenation catalyst, which, in addition, should have a long service life.

SUMMARY

We have now found that, in the catalytic gaseous phase dehydrogenation of completely and/or partially hydrogenated hydroxydiphenyl, in the presence of dehydrogenation catalysts containing nickel, chromium aluminum, copper and alkali sulphate and/or alkali carbonate, the service life of these dehydrogenation catalysts can be considerably lengthened by using as a starting material compounds or mixtures of compounds to which compounds corresponding to the general formula (I):

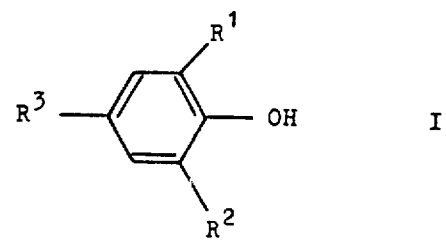

in which
$R^1$, $R^2$ and $R^3$, which are the same or different, each represents a linear or optionally branched alkyl radical having up to 6 carbon atoms, in addition to which $R^3$ can also represent hydrogen,
are added as stabilisers before they are exposed for the first time to air and/or other oxygen-containing gases.

DESCRIPTION

Examples of radicals $R^1$, $R^2$ and $R^3$ are methyl, ethyl, propyl, isopropyl, butyl, isobutyl, tert.-butyl, the isomeric pentyl and hexyl radicals. The following are mentioned as examples of the stabilisers which can be used in the process according to the invention:

2,6-dimethyl-p-cresol, 2,6-dimethylphenol, 2,6-diethyl-p-cresol, 2,6-diisopropyl-p-cresol, 2,6-di-tert.-butyl-p-cresol and 2,6-di-tert.-butyl-p-ethylphenol, of which 2,6-di-tert.-butyl-p-cresol is particularly preferred.

According to the invention, the aforementioned stabilisers are generally added to the compounds or mixtures of compounds comprising completely and/or partially hydrogenated hydroxydiphenyl, which are used for dehydrogenation, in a quantity of less than 0.1% by weight of the total starting material. They are preferably added in a quantity of from 0.01% by weight to 0.09% by weight and, in particular, in a quantity of from 0.02 to 0.05% by weight.

Apart from their influence, according to the invention, upon the stability of the starting material and the service life of the dehydrogenation catalyst used, these small quantities of stabiliser generally have no negative effect upon the quality of the dehydrogenation product so that they do not have to be subsequently removed. If, however, their subsequent removal is required, for example, in order to obtain a particularly pure hydroxydiphenyl, they can be removed by purification processes known per se, for example by the process described in DOS No. 2,102,476. In this process, the stabiliser accumulates during distillation in the first runnings and during crystallisation in the mother liquor, and can be removed with them.

Starting compounds for the process according to the invention which are stabilised during the period of storage preceding their use and during their use by the addition of stabilisers of general formula (I) in accordance with the invention, are for example:

2-cyclohexylidene cyclohexanone,
2-cyclohexenyl cyclohexanone,
2-cyclohexyl cyclohexanone,
2-cyclohexyl cyclohexanol,
2-cyclohexylphenol,
3-cyclohexylphenol,
4-cyclohexylphenol,
2-phenylcyclohexanone, and
2-phenylcyclohexanol.

These compounds are known and are readily obtainable. Thus, 2-cyclohexylidene cyclohexanone and 2-cyclohexenyl cyclohexanone, for example, are obtained by condensing cyclohexanone in the presence of acid or basic catalysts by conventional methods. In addition, these two compounds are formed alongside 2-cyclohexyl cyclohexanone, 2-cyclohexyl cyclohexanol etc. as secondary products in the catalytic dehydrogenation of cyclohexanol. They can readily be separated off from the dehydrogenation mixture by distillation and can be used in admixture for the production of 2-hydroxydiphenyl.

Cyclohexylphenol is obtained in accordance with known methods by the catalytic alkylation of phenol. In addition, 2-cyclohexylphenol is formed as a secondary product alongside 2-phenyl cyclohexanone and 2-phenyl cyclohexanol, 2-cyclohexyl cyclohexanol and 2-cyclohexyl cyclohexanone in the synthesis of 2-hydroxydiphenyl.

Compounds of general formula (I) which can be used as stabilisers in the process according to the invention are also known.

The addition of these compounds, in accordance with the invention, to the starting material, which has preferably been prepared in the absence of air and/or other oxygen-containing gases or purified by distillation in the absence of such gases, is carried out as known per se.

The stabilisers can be added to the starting material in the required quantity either continuously or in batches, for example after preparation or distillation, for example by introduction, pouring in, stirring in or by other measures known per se, followed by thorough admixture and/or dissolution, for example by stirring, shaking, ultrasonics or other methods known per se. However, it is also possible to add in batches to a certain quantity of stabiliser the quantity of starting material required to obtain the required concentration, for example by distillation, followed by thorough admixture and/or dissolution as described above, or alternatively a correspondingly selected component stream of the stabiliser can be added, for example, to a liquid or gaseous stream of the starting material and the two streams can be thoroughly admixed by suitable measures, for example by generating turbulence in the main stream, tangentially introducing the side stream or installing a mixing chamber.

In general, the process according to the invention is carried out by passing the starting material stabilised in accordance with the invention in the vapour phase over dehydrogenation catalysts known per se and prepared, for example, by the process described in DOS No. 2,049,809 or in DOS No. 2,146,052, as known per se at temperatures of from 300° to 400°C, more particularly at temperatures of from 320° to 350°C under normal or reduced pressure.

The resulting crude hydroxydiphenyl can be used directly or after it has been purified. Purification can be carried out by methods known per se, for example by distillation and/ or crystallisation. Crude o-hydroxydiphenyl is best purified by the process described in DOS No. 2,102,476.

o-Hydroxydiphenyl is a known preservative for citrus fruits and is also used in known manner as a carrier for dyeing with dispersion dyes.

It is surprising that, by using a starting product stabilised with compounds of formula (I) in accordance with the invention, the activity of the dehydrogenation catalyst used remains intact much longer than is the case where a non-stabilised starting product is used. Although the stabilising effect of compounds of formula (I) against the action of oxygen-containing gases is known, per se, their influence through the starting product stabilised in accordance with the invention on the activity and service life of the dehydrogenation catalysts was neither known nor obvious, especially since it cannot be obtained with similar compounds of the kind present to some extent in the starting material normally used, for example o-cyclohexylphenol.

This effect of stabilisation, which is crucial to the process of the invention, affords a number of advantages to the aforementioned dehydrogenation process which represent a considerable improvement over the prior art. These advantages over the prior art include, for example, the fact that, by virtue of its longer service life, the catalyst does not have to be renewed as early as it did before, and the fact that, on the other hand, there is no longer any need for catalyst regeneration which would interrupt the continuous dehydrogenation process and, hence, would also result in breaks in production.

Another advantage is, for example, the fact that the reaction product has a more uniform composition over much longer periods of operation, which makes the product much simpler and less expensive to purify.

The percentages quoted in the following Examples relate to weight unless otherwise stated.

EXAMPLES

A catalyst prepared as follows in accordance with DOS No. 2,049,809 was used in the following Examples:

8580 g of a catalyst starting material containing 42.7% by weight of nickel, 9.5% by weight of chromium, 3.2% by weight of aluminium and 0.2% by weight of copper, obtained as known per se by precipitating a carbonate-hydroxide mixture containing the elements nickel, aluminium and copper from an aqueous solution comprising the corresponding nitrates and sulphates (50% : 50%) with sodium carbonate solution, and subsequently reacting the precipitate, after it had been washed, with ammonium bichromate solution, are made into a paste in a solution of 225 g of potassium sulphate in 7900 ml of water. The resulting catalyst paste is dried at 120°C, ground and mixed with 3% of graphite and the resulting mixture is processed in a tabletting press into tablets 5 mm in diameter and approximately 4–6 mm thick.

1000 g of the tablets thus obtained are treated for 2.5 hours at 390°C with 100 litres of hydrogen per hour and then for 6 hours at around 20° to 40°C with 100 litres/hour of a mixture of 2% by volume of air and 98% by volume of $CO_2$.

The tablets are then ground up and mixed with 2% of graphite, and the resulting mixture is re-tabletted, reduced for 2.5 hours at 390°C with 730 litres of hydrogen per hour and subsequently tempered in a $CO_2$-atmosphere for 30 hours at 100°C:

| Powder density: | 1.16 g/ml |
| --- | --- |
| Specific surface: | 136 m²/g |
| Ni (metallic): | 25.6%, Ni (total) 56.2%. |

In all the Examples, the process was carried out as described below:

Using a vertically arranged tube reactor approximately 550 mm long with a tube diameter of 17 mm, which is filled with 30 ml of the catalyst prepared as described above and the upper part of which serves as an evaporation zone, 6.0 g/h of a mixture of 2-cyclohexenyl cyclohexanone and 2-cyclohexylidene cyclohexanone, hereinafter referred to as dianone, obtained by condensing cyclohexanone in the presence of an ion-exchange resin containing sulphonic acid groups, followed by distillation (cf. Chem. Abstr. 75,5344 y (1971), are introduced at 330°C at the upper end of the reactor and the reaction product is run off from the lower end of the reactor.

EXAMPLE 1

0.1% of 2,6-di-tert.-butyl-p-cresol was added to a dianone immediately after preparation before contact with air, followed by stirring for 8 hours at 50°C in the presence of air. The product has an acid number of from 0.4 to 0.5.

After a start-up period of a few hours, the reaction product contains:
 82 % of 2-hydroxydiphenyl,
 7 % of 2-cyclohexylphenol and 2-phenyl cyclohexanone,
 1 % of 2-cyclohexyl cyclohexanone and dianone,
 5.5% of diphenylene oxide, and
 3.5% of diphenyl.

After 1300 hours' operation, the reaction product contains:
 70 % of 2-hydroxydiphenyl,
 19 % of 2-cyclohexylphenol and 2-phenyl cyclohexanone,
 3 % of 2-cyclohexyl cyclohexanone and dianone,
 4 % of diphenylene oxide, and
 2 % of diphenyl,
and, after a further 1300 hours,
 65 % of 2-hydroxydiphenyl,
 22 % of 2-cyclohexylphenol and phenyl cyclohexanone,
 7 % of 2-cyclohexyl cyclohexanone and dianone,
 3.5% of diphenylene oxide, and
 1.5% of diphenyl.

EXAMPLE 2 (comparison Example)

A dianone is used which, although having been stored in a closed vessel after preparation, had not been completely protected against air during storage and handling. The product has an acid number of 0.3.

After a start-up period of a few hours, the reaction product contains:
 81 % of 2-hydroxydiphenyl,
 7 % of 2-cyclohexylphenol and 2-phenyl cyclohexanone,
 2 % of 2-cyclohexyl cyclohexanone and dianone,
 4 % of diphenylene oxide,
 3 % of diphenyl, and
 3 % of other products.

After approximately 1000 hours' operation, however, the reaction product contains:
 65 % of 2-hydroxydiphenyl,
 22 % of 2-cyclohexylphenol and 2-phenyl cyclohexanone,
 5 % of 2-cyclohexyl cyclohexanone and dianone, and
 2.5% of diphenyl,
and, after a further 800 hours,
 60 % of 2-hydroxydiphenyl,
 24 % of 2-cyclohexylphenol and 2-phenyl cyclohexanone,
 8 % of 2-cyclohexyl cyclohexanone and dianone,
 3.5% of diphenylene oxide, and
 2 % of diphenyl.

EXAMPLE 3 (comparison Example)

A dianone is used which had been in contact with air for 8 hours at room temperature while stirring. The product has an acid number of 0.5.

After a start-up period of a few hours, the reaction product contains:
 77 % of 2-hydroxydiphenyl,
 7 % of 2-cyclohexylphenol and 2-phenyl cyclohexanone,
 6 % of 2-cyclohexyl cyclohexanone and dianone,
 6 % of diphenylene oxide, and
 2 % of diphenyl,
and, after 500 hours' operation,
 58 % of 2-hydroxydiphenyl,
 23 % of 2-cyclohexylphenol and 2-phenyl cyclohexanone,
 8 % of 2-cyclohexyl cyclohexanone and dianone,
 4.5% of diphenylene oxide, and
 2 % of diphenyl.

EXAMPLE 4 (comparison Example)

A dianone is used which had been in contact with air for 8 hours at 50°C while stirring. The product has an acid number of 5.7.

A reaction product, the 2-hydroxydiphenyl content of which falls over 200 hours from 69 to 49%, is obtained.

What is claimed is:
1. In the process for the production of hydroxydiphenyl, which comprises dehydrogenating a starting material comprising completely or partly hydrogenated hydroxydiphenyl in the gaseous phase in the presence of a dehydrogenation catalyst containing nickel, chromium, aluminum, copper and an alkali compound selected from the group of alkali metal sulfate and alkali metal carbonate, the improvement which comprises adding a stabilizer having the formula (I):

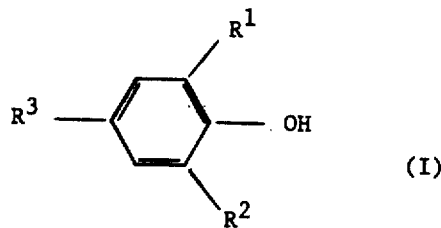

(I)

wherein:

R$^1$, R$^2$ and R$^3$, which may be the same or different, each represents a linear or optionally branched alkyl radical having up to 6 carbon atoms, in addition to which R$^3$ can also represent a hydrogen atom, to the starting material before it comes into contact for the first time with oxygen-containing gases and the dehydrogenation catalyst.

2. Process of claim 1 wherein the formula (I) compound is 2,6-di-tert.-butyl-p-cresol.

3. Process of claim 1 wherein the formula (I) compound is added in a quantity of less than 0.1% by weight.

4. Process of claim 1 wherein the formula (I) compound is added in a quantity of from 0.01 to 0.09% by weight.

5. Process of claim 1 wherein the formula (I) compound is added in a quantity of from 0.02 to 0.5% by weight.

* * * * *